(12) United States Patent
Kaselis

(10) Patent No.: US 6,657,720 B1
(45) Date of Patent: Dec. 2, 2003

(54) SPECTROMETER ATTACHMENTS AND PHOSPHORESCENCE DECAY MEASUREMENT

(75) Inventor: Martin Kaselis, Ringwood (AU)

(73) Assignee: Varian Australian Pty LTD, Mulgrave (AU)

( * ) Notice: Subject to any disclaimer, the term of this patent is extended or adjusted under 35 U.S.C. 154(b) by 0 days.

(21) Appl. No.: 09/831,244
(22) PCT Filed: Sep. 6, 2000
(86) PCT No.: PCT/AU00/01058
§ 371 (c)(1), (2), (4) Date: Jul. 2, 2001
(87) PCT Pub. No.: WO01/18529
PCT Pub. Date: Mar. 15, 2001

(30) Foreign Application Priority Data

Sep. 8, 1999 (AU) .............................................. PQ2705

(51) Int. Cl.⁷ .......................... G01N 21/64; G01K 11/32
(52) U.S. Cl. .................... 356/317; 356/318; 250/458.1
(58) Field of Search ................................ 356/317–318; 250/458.1, 459.1

(56) References Cited

U.S. PATENT DOCUMENTS

| | | | | |
|---|---|---|---|---|
| 3,861,004 A | * | 1/1975 | Schenk | 403/408.1 |
| 4,426,147 A | * | 1/1984 | Shiozawa et al. | 396/63 |
| 5,039,219 A | * | 8/1991 | James et al. | 356/318 |
| 5,107,445 A | * | 4/1992 | Jensen et al. | 374/161 |
| 5,600,147 A | * | 2/1997 | Jensen | 250/458.1 |
| 5,783,926 A | * | 7/1998 | Moon et al. | 320/106 |
| 5,859,522 A | * | 1/1999 | Theobald | 320/106 |
| 5,948,077 A | * | 9/1999 | Choi et al. | 710/9 |

FOREIGN PATENT DOCUMENTS

| | | | |
|---|---|---|---|
| DE | 32 03 381 | * | 8/1983 |
| EP | 394 074 | * | 10/1990 |
| EP | 437 697 | * | 7/1991 |
| FR | 2 638 211 | * | 4/1990 |
| WO | 84/00926 | * | 3/1984 |

* cited by examiner

Primary Examiner—Thong Nguyen
(74) Attorney, Agent, or Firm—Edward H Berkowitz

(57) ABSTRACT

A spectrometry instrument, e.g., for time-resolved spectroscopy, has quick-change exchangeable accessories (48, 50, 52) which are manually attached via rotation of a camming means to engage and lock a stud member. A circuit element in each accessory (48, 50, 52), such as a resistor or a configured pin connection, acts to generate a voltage in the instrument that uniquely identifies which accessory is attached. A method for measuring a phosphorescence decay characteristic includes applying an excitation pulse to a sample (34); obtaining emission intensity data for a sequence of time delays following the excitation pulse; repeating for at least one further excitation pulse using a different sequence of time delays; and interleaving the data from different excitation pulses to construct a decay characteristic.

14 Claims, 6 Drawing Sheets

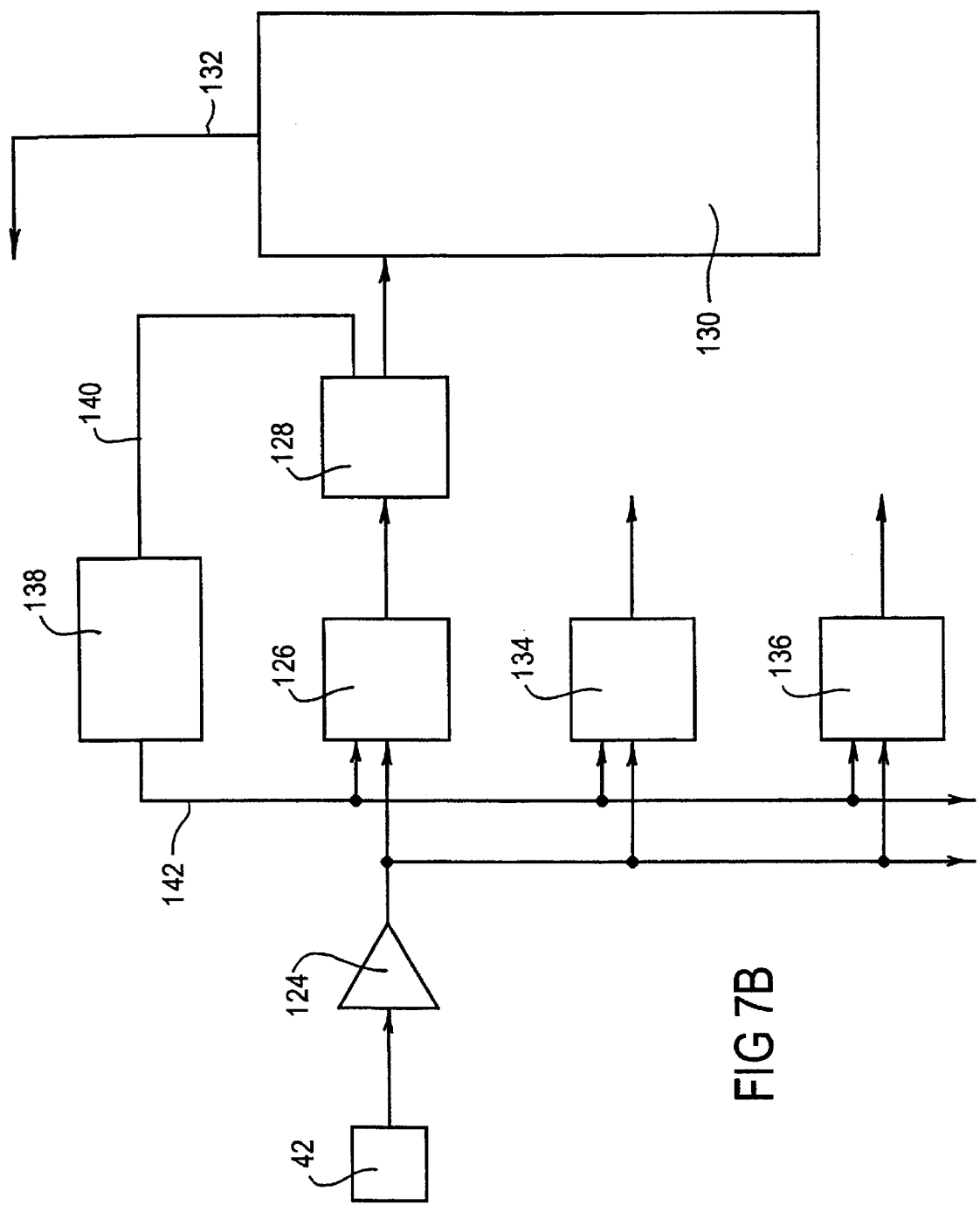

SPECTROMETER ATTACHMENTS AND PHOSPHORESCENCE DECAY MEASUREMENT

TECHNICAL FIELD

This invention relates to spectrometry instrumentation in general and in particular examples to fluorescence, phosphorescence and luminescence spectrophotometry.

BACKGROUND

A fluorescence spectrophotometer usually comprises a flash light source, an excitation monochromator or filter, a sample cell containing a sample to be analysed, an emission monochromator or filter, a photodetector and signal processing electronics. A specific wavelength of light from the flash source, as selected by the excitation monochromator or filter, is directed into the sample cell and resultant fluorescence light from the sample enters the emission monochromator or filter. A specific wavelength of the fluorescence light, as selected by the emission monochromatolr or filter, is directed onto the photodetector to produce an electrical signal corresponding to the intensity of the fluorescent light. Such an instrument may be arranged to make a fluorescence, phosphorescence or luminescence measurement. Fluorescence measurements relate to light which is emitted virtually immediately by a sample upon its exposure to the excitation light, whereas phosphorescence measurements relate to the light emitted from the sample a short characteristic time after its exposure to the excitation light. Luminescence measurements are taken by measuring the emitted light from a sample without exposing the sample to excitation light. Such measurements are used to characterise substances, with fluorescence measurements in particular having wide application in the biotechnical field for characterising DNA and other proteins, for example using fluorofors.

It is known in spectrometry instruments in general, and in spectrophotometers for fluorescence, phosphorescence and luminescence measurements, to provide exchangeable accessories. Generally these may provide different sample presentation facilities, for example a liquid sample presentation accessory may be exchanged for one which provides for presentation of a solid state sample. Different accessories may also provide for temperature control of samples via Peltier, Dewar or other cryostat devices, successive feeding of multiple samples to a reading location, or multiple sample carriers such as a well plate and reader therefor.

In order not to compromise test results, it is important that the exchangeable accessories for a spectrometer be repeatably and accurately locatable on the instrument. Prior art arrangements for doing this, which involve screw threaded attachment of one part to another, generally do not facilitate rapid exchange of one accessory for another.

As described above, the capability to make phosphorescence measurements (that is, phosphorescence emission intensity versus time) is included in some fluorescence spectrophotometers. To collect phosphorescence intensity versus time data that results from a short pulse of excitation light, it is necessary to repetitively measure the emission intensity at a time short enough to adequately define the relationship. The capturing of a data point can be done relatively quickly via a sample and hold circuit, however the measurement and digitisation of that data point typically takes a reasonable length of time. Such data conversion often takes longer than the required interval between successive measured points. By way of example, adequate definition of the emission time relationship may require measurement of the emission intensity at 1 microsecond intervals yet the digitisation of a single emission datum may take, say, 19.5 microseconds. For this reason, the prior art technique is to use a sampling approach. In this arrangement, the excitation light pulse is generated repetitively at a constant interval. The interval must be long enough for the emission from one pulse to have fallen substantially to zero before the next pulse is applied. After each excitation pulse a single emission intensity is measured at a controlled time after the excitation pulse so as to give a single datum of the emission time relationship. For each successive cycle the time interval between the excitation and capturing of emission intensity is modified so as to build up a complete picture of the overall emission versus time relationship. In the example given. for the first cycle the time delay could be 1 microsecond. For the second cycle the time delay may be 2 microseconds. For the third the delay will be 3 microseconds and so on.

The problem with this approach is that the interval between excitation pulses must be long enough to allow the emission to die away substantially to zero between one pulse and the next. At the same time many cycles are needed to build up a comprehensive picture of the emission versus time relationship. The overall measurement is thus slow. For example, again referring to the above example of one microsecond intervals between data points, if data covering two milliseconds is desired then 2000 data points will need to be collected. If the time for the emission to substantially fall to zero is 10 milliseconds, it will take 20 seconds to complete the 2000 measurement cycles.

SUMMARY OF THE INVENTION

According to a first aspect the presen1t invention provides a spectrometry instrument and an exchangeable accessory therefor including a manually operable mechanism for attaching the exchangeable accessory to the instrument, the mechanism including a manually rotatable camming means associated with one of the accessory or the instrument, a male member associated with the other of the accessory or the instrument, the male member having a camming surface which is engageable by the camming means, wherein the accessory is positionable on the instrument in a predetermined location and the camming means is manually rotatable to engage the camming surface of the male member and thereby lock the accessory on the instrument in the predetermined location.

In spectrometry instruments which have exchangeable accessories, it would be advantageous if the instrument could detect if an accessory has been attached and if so, to identify what accessory it is. The advantages of this include the instrument's set up and programming for use with a particular accessory being able to be automatically established. Also for those accessories that include electrical componentry, such as stepper motors, it would be advantageous to detect the presence of such a component.

According to a second aspect the present invention provides a spectrometry instrument including an electrical circuit for identifying anyone of a plurality of exchangeable accessories which are connectable to the instrument, the electrical circuit including a voltage source and means for generating an identifying voltage therefrom, wherein each accessory includes at least one circuit element such that connection of an accessory to the instrument alters the identifying voltage to a value which is uniquely dependent upon the accessory which is connected to the instrument.

The accessory recognition circuitry may be such that it recognises the presence of an electric motor of an accessory. In this case a voltage divider can be arranged to provide a logic high signal in the presence of a motor by virtue of the motor winding completing a circuit between the voltage source and the voltage divider. In the absence of the motor, the circuit is open and a logic low signal is derived from the voltage divider.

Preferably the spectrometer includes circuitry for identifying an accessory and further circuitry for determining the presence or absence of an electric motor in that accessory.

For a spectrometer with a capacity to have a number of different accessories connected thereto at the same time, each connection socket for each accessory may include accessory recognition circuitry as above described. In this arrangement, the signal line for the identifying voltage from each circuit may be connected to a multiplexer for input to a microprocessor of a computer.

In a third aspect the present invention provides a method and apparatus for reducing the time for measuring a number of data points for determining a phosphorescence decay characteristic (that is, phosphorescence emission intensity versus time) of a sample.

According to this third aspect, there is provided a method of determining a phosphorescence decay characteristic of a sample or at least a portion thereof, including i) exposing the sample to a first excitation flash of light,
ii) measuring the intensity of a decaying phosphorescence light signal from the sample caused by the first excitation flash at each of a sequence of measurement points which commence a controlled time after the first excitation flash and are separated by controlled times,
iii) exposing the sample to a second excitation flash of light and
iv) measuring the decaying phosphorescence light signal from the sample caused by the second excitation flash at each of a sequence of measurement points which commence a controlled time after the second excitation flash and are separated by controlled times, wherein the time instants to the first and subsequent measurement points from the second excitation flash lie between the first and subsequent measurement points respectively from the first excitation flash,
v) assembling the phosphorescence measurements into time sequence to produce a phosphorescence decay (characteristic, or a portion thereof, for the sample.

The assembly of the phosphorescence measurements into time sequence results in the measured data points from the second excitation flash being interleaved with those from the first excitation flash.

In some cases as the phosphorescence emission from a sample decays, the time interval between the data points which is required to adequately define the phosphorescence characteristic becomes longer. The above described method, in relating to determining possibly only a portion of a phosphorescence decay characteristic, recognises that after a certain time, the necessary time interval between data points to adequately define the characteristic may be so long as to be able to be sequentially measured from the emission caused by one of the excitation flashes and not both. Thus the above described method may be applied only for determining an initial or any particular predetermined portion of a decay characteristic.

The time intervals in step (ii) established by the controlled times are greater than the measurement and digitisation time. These intervals may be controlled in the sense they are prior determined or computed during the data collection process (that is, they are computed "on the fly" from the time for measurement and digitisation of data). The time intervals between measured data points may be uniform or vary from one interval to the next. Similarly, the time intervals in step (iv) established by the controlled times may be prior determined or determined by computation during the data collection process.

The method may be extended wherein further excitation flashes are initiated and further phosphorescence emission intensity measurements taken which result from each such further excitation flash, the further phosphorescence measurements for each such further excitation flash being taken at controlled times (ie., prior determined or computed times as above described) such that each such further phosphorescence measurement can be interleaved between phosphorescence measurements resulting from earlier excitation flashes. That is, steps (iii) and {iv) may be repeated as often as necessary until all required measured points are obtained.

According to this third aspect of the invention there is also provided apparatus for performing the above described method. This apparatus comprises a spectrophotometer and means for controlling the spectrophotometer, said means for controlling being such as to acquire sequential phosphorescence emission measurements data from each of a number of excitation cycles applied to a sample in the spectrophotometer and to assemble that data into a correct time sequence to define a phosphorescence decay characteristic, or a portion thereof, for the sample.

The means for controlling the spectrophotometer may be a suitably programmed computer or a dedicated device or circuitry.

Preferably this apparatus includes a manually operable mechanism for attaching an exchangeable accessory as described herein above. The apparatus also preferably includes an accessory recognition circuit as also described hereinabove.

The following detailed description with reference to drawings is provided to give a better understanding of the invention and to show how it may be carried into effect in all its aspects. This description and the drawings are given by way of non-limiting example only and are not to be interpreted as limiting the generality of the preceding description.

BRIEF DESCRIPTION OF DRAWINGS

FIGS. 7A and 7B illustrate data acquisition circuits; and

DESCRIGTION OF PREFERRED EMBODIMENTS

Figure 1:
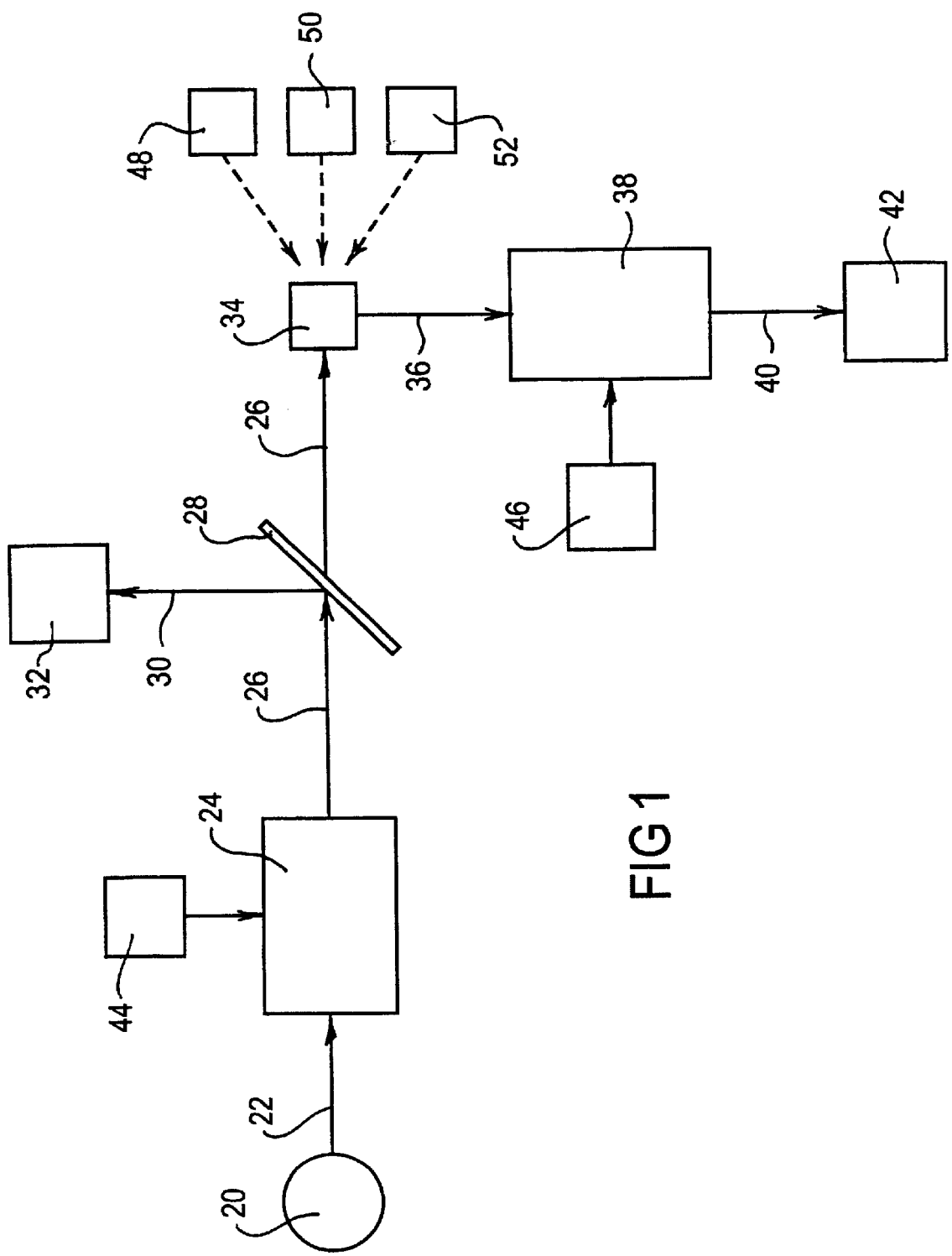
FIG. 1 diagrammatically illustrates a spectrophotometer for measuring fluorescence or phosphorescence from a sample.

A fluorescence spectrophotometer, as diagrammatically illustrated in FIG. 1, includes a Xenon flash light source 20, the light 22 from which is directed into an excitation monochromator 24. Light 26 of a selected wavelength which exits monochromator 24 passes through a beam splitter 28 to derive a reference beam 30 the intensity of which is measured by a detector 32. Excitation light 26 continues from beam splitter 28 and irradiates a sample in sample holder 34. The fluorescence (or phosphorescence) light 36 emitted by the sample traverses an emission monochromator 38, the light of a selected wavelength 40 of which the intensity is measured by detector 42. The emission monochromator is arranged to be off the axis of the excitation monochromator 24. Drivers 44 and 46 for each of the monochromators 24, 38 respectively, allow for wavelength, filter and slit width selection.

Operation of the spectrophotometer is controlled by a computer or other means (not shown in FIG. 1) such that slit: widths and filters are selectable according to wavelength and controlled by stepper motors allowing either manual or automatic selection. Slit selector is user controlled. The computer or other control means also controls the data acquisition electronics (to be described below) and the manipulation of the data, notably for phosphorescence measurements, also to be described below.

The detectors 32 and 42 are photomultiplier tubes. If the light tight sample compartment door of the instrument is opened allowing incident light to reach the photomultiplier tubes 32 and 42, the firmware recognises this overrange condition and causes a filter to be moved to block the entry of the incident light into the photomultiplier tubes and/or reduce the EHT power supply. Another protection feature is that monochromators 24 and 38 include safety interlocks for preventing a zero order setting for slit widths greater than 5 nm. The instrument includes exchangeable accessories schematically represented at 48, 50 and 52. Such accessories generally provide for different samples and sample presentation regimes and are thus exchangeable in relation to the sample holder 34. The instrument may simultaneously have a number, for example up to four, different accessories connected thereto. All accessories require mechanical attachment to a sample compartment of the instrument and in one aspect this invention provides a quick, simple and reliable attachment mechanism for this. The sample compartment of a spectrometer is an accessible space within the spectrometer wherein a sample is conveniently placed for the purpose of making spectrometric measurements. A sample compartment is typically provided with means to hold a sample in a precisely defined position with respect to the paths of light beams in the spectrometer, and is provided with apertures for the passage of said light beams. In another aspect the invention provides electrical means for detecting the presence or absence of an accessory, and if an accessory is attached and plugged in, identifying that accessory so that appropriate software programmes for measurement regimes using that accessory may be automatically loaded. This saves user time in that the user does not then have to search for the relevant programmes.

Figure 2:
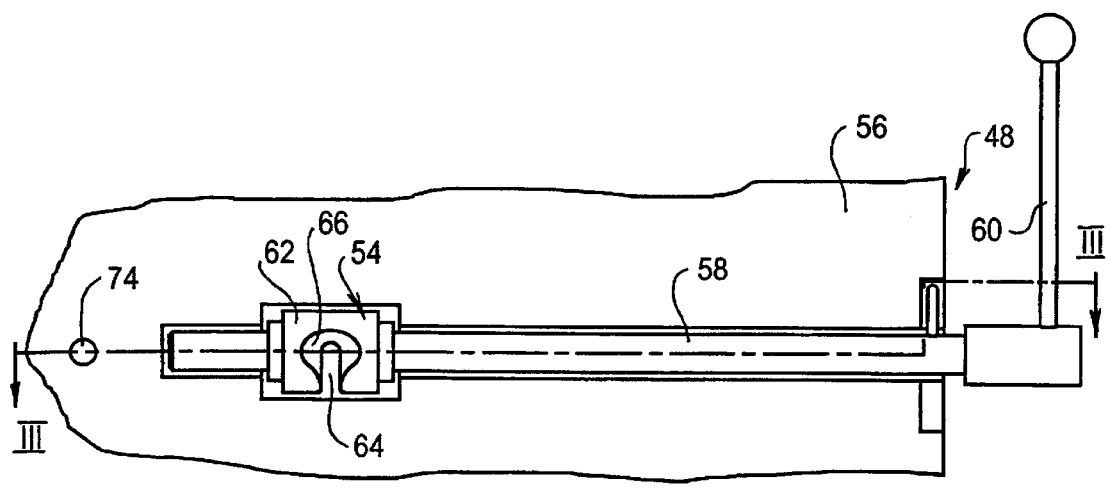
FIGS. 2 to 4 illustrate a manually operable mechanism for attaching an accessory to a spectrophotometer.
Figure 3:
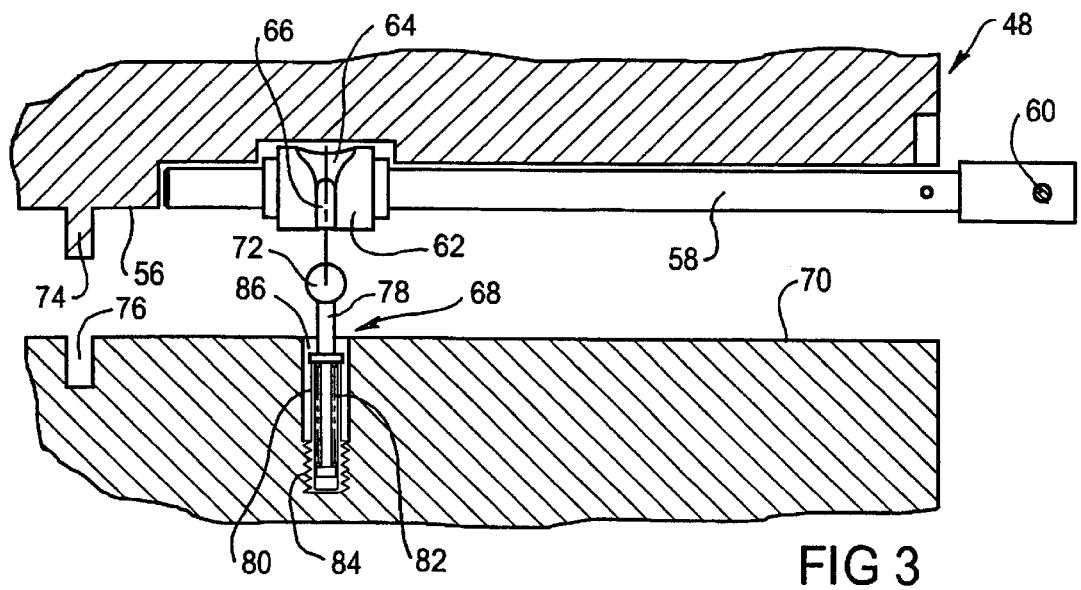
Figure 4:
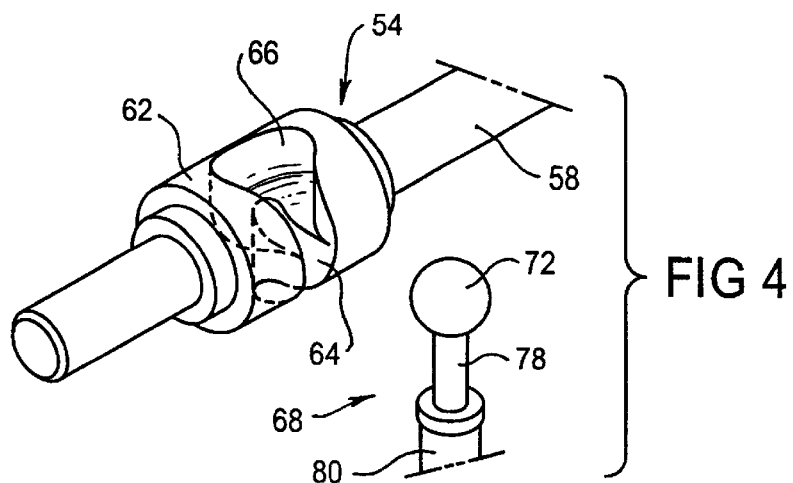

With reference to FIG. 24, the mechanical attachment mechanism for an accessory such as 48 comprises a manually rotatable camming means 54 associated with the accessory 48. FIG. 2 shows an underneath view of the base 56 of an accessory 48 on which is mounted for rotation a shaft 58 for manually rotating the camming means 54 via a handle 60 (a plate which is attachable to the base 56 for covering the shaft 58 has been omitted from FIGS. 2 and 3). FIG. 3 shows a section of FIG. 2 on line III—III.

Ideally the camming means is rotated through less than 360° to attach the accessory and more ideally its rotation is about 180°. Preferably the camming means has a female form for receiving the male member, for example it may be spherical or cylindrical with a recess formed therein having a curved camming surface which interacts with the camming surface of the male member. The camming means is preferably located substantially centrally of a base of the accessory and is operable via a shaft which extends to a peripheral surface of the accessory for manual operation.

Preferably the shaft includes a handle or knob for facilitating its manual rotation.

Preferably the male member is associated with and is biased in a direction towards the instrument such that, as the camming means and the male member become engaged, the male member is moved in a direction away from the instrument against the bias. This ensures that when the camming means and the male member are fully engaged to lock the accessory onto the instrument, a positive holding force is maintained on the accessory.

Alternatively the camming means may be associated with the instrument and the male member with the accessory.

Preferably the accessory and the instrument include a number of complementary projections such as pins on and recesses in their facing surfaces for establishing the predetermined location for the accessory on the I instrument. Thus, as the camming means is rotated to engage the male member and draw the accessory towards the instrument, the projections, which are preferably on the accessory, locate in complementary recesses which are preferably in the instrument, to ensure the correct location of the accessory on the instrument.

It will be appreciated that embodiments of the invention as described above and to be described in more detail below provide an easily manually operable attachment mechanism which allows quick attachment and release of an accessory from a spectrometry instrument which is preferably a spectrophotometer. This quick attachment and release advantage of the invention is derived from the mechanism's use of a single attachment point and the actual attachment being achieved by an approximate half turn of the camming means via a prominently accessible handle, knob or the like.

The camming means 54 comprises a cylinder 62 within which a recess 64 is formed which provides a curved camming surface 66.

A male member 68 (see FIG. 3) is mounted in the base 70 of the sample compartment of the instrument and includes an outer spherical form 72 which is engageable by the camming means 54, specifically its camming surface 66, whereby rotation of the camming means 54 via handle 60 causes its surface 66 to interact with spherical surface 72 of male member 68 to draw the accessory base 56 into facing contact with instrument blase 70 and lock the accessory on the instrument in a predetermined location. The predetermined location is determined by the relative locations of the camming means 54 and the male member 68 and by complementary location means on an accessory and the instrument. These complementary location means may comprise protrusions 74 on the accessory base 56 (only one of which is shown in FIGS. 2 and 3) which are locatable in recesses 76 in the instrument base 70. A convenient and preferred mechanism for spatially locating the accessory in the sample compartment is to use a kinetic mount. This consists of three protruding pegs on either the instrument or the accessory The first peg engages in a hole in the mating surface and thereby accurately locates one point of the accessory to the instrument. Height control may be achieved either by the peg resting on the bottom of a blind hole or a shoulder on the peg resting on the top of the hole. The second peg locates in a slot in the mating surface whose centre line passes through the centre of the previously mentioned hole. It uses similar means of height control as for the first peg. This controls angular position of the accessory with reference to the first location point. The third peg rests on a plate on the mating surface.

The spherical form 72 of the male member 68 is at the end of a stem 78 mounted in a sleeve 80 and biased inwardly relative thereto by a spring 82. The sleeve 80 is screw-threaded at a lower 01" inner end 84 for attachment in an aperture 86 in the base. Thus as the camnning means 54 engages the male member 68 and is rotated relative thereto the spring 82 acts to bias the spherical form 72 downwardly towards the base 70 of the instrument. This ensures that when the camming means 54 and the male member 68 (specifically the surfaces 66 and 72) are fully engaged to lock the accessory 48 onto the instrument, a positive holding force maintained on the accessory.

The accessory 48 is releasable simply by reversely manually rotating the handle 60 to release the spherical form 72 from the camming surface 66 and lifting the accessory away.

Figure 5:
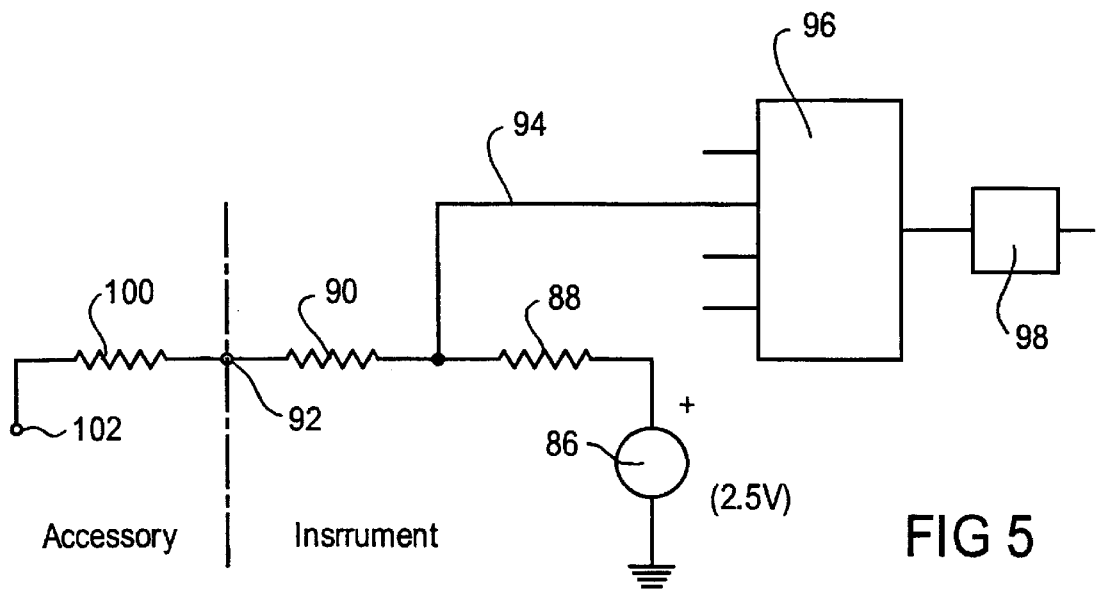
FIGS. 5 and 6 illustrate accessory recognition circuitry for use in a spectrophotometer.

The spectrophotometer includes a number of sockets, for example four, .in its sample compartment for receiving plugs on the accessories, that is, each accessory has a plug which is receivable in anyone of the four sockets. An accessory recognition circuit in the spectrophotometer includes a voltage source 86 (see FIG. 5) the negative side of which is connected to ground and the positive to a means for generating an identifying voltage in the form of a voltage divider comprising resistors 88 and 90. The series connection of the source 86 and resistors 88 and 90 is connected to a dedicated pin 92 of a socket in the sample compartment. A signal line 94 is connected between the resistors 88 and 90 and a multiplexer 96, and then to an analog to digital converter 98 and a microprocessor (not shown) for reading the data and controlling operations. An identifying voltage for an accessory is read via signal line 94. If there is no accessory present, this circuit is open and the voltage of source 86 is read on line 94.

Preferably the means for generating an identifying voltage is a voltage divider and this together with the voltage source provide an open electrical circuit such that in the absence of an accessory the identifying voltage floats to the voltage of the voltage source, thereby identifying the absence of an accessory. Preferably each accessory provides a circuit element for completing the electrical circuit of the spectrophotometer when connected thereto. The circuit element of each accessory is different such that when it completes the circuit including the voltage source and the voltage divider of the spectrometer, it causes the identifying voltage to change to a value which is unique for that accessory. The identifying voltage which is generated is read by a microprocessor which identifies the particular accessory, or absence of an accessory 1 connected to the spectrometer, which is preferably a spectrophotometer.

The circuit element of an accessory, may simply provide a link which connects to ground, or a particular voltage of the instrument, e.g. +5V, +12V, +15V or −15V, depending on the accessory. This arrangement can be used for accessories which do not include their own electronics. For accessories which do include their own electronics and thus a circuit board and a plurality of circuit elements, a resistor may be included which connects between the circuit of the instrument and a connection to ground. +5V, +12V, +15V or −15V. It will be evident that a number of circuit combinations are possible to provide for a number of different accessories. For example, a circuit element of an accessory in the form of a link that connects to ground, +5V, +12V, +15V or −15V gives 5 combinations. That is, it gives the possibility of generating five unique voltages and thereby the identification of five different accessories.

Connection of an accessory to the socket may provide a circuit element in the form of a link (not shown) to ground, or to an analog voltage, say +5 volts, +12 volts, +15 volts or −15 volts on other pirls of the socket, depending on the particular accessory. When such a link is made, the voltage appearing on line 94 will alter to a value which is uniquely dependent upon the particular link established by that accessory. Thus the vol1age signal on line 94 can be used by the microprocessor to identify a particular accessory. Such a link for completing the circuit of the instrument is suitable for accessories which do not include their own circuitry. Furthermore the possibility of the link connecting to ground, +5 volts, +12 volts, +15 volts or −1 Ei volts provides five combinations, that is, it allows the identification of five different accessories.

The multiplexer includes four signal inputs, one from each of a circuit such as is illustrated associated with each of 1the four accessory sockets.

Alternatively where an accessory does include its own circuitry, a resistor 100 may be added which is connectable, via the plugging in of an accessory to one of the instrument sockets, to ground or ~3 supply voltage such as +5 volts, +12 volts, +15 volts or −15 volts at pin 102. This will also alter the voltage on signal line 94 to a unique value for the particular accessory concerned. This allows more combinations for the identifying voltages 94 than the previous arrangement of using only a link. Alternatively the resistor 100 may be connected to or replaced by a programmable voltage source to allow for re-configurable accessories.

Figure 6:
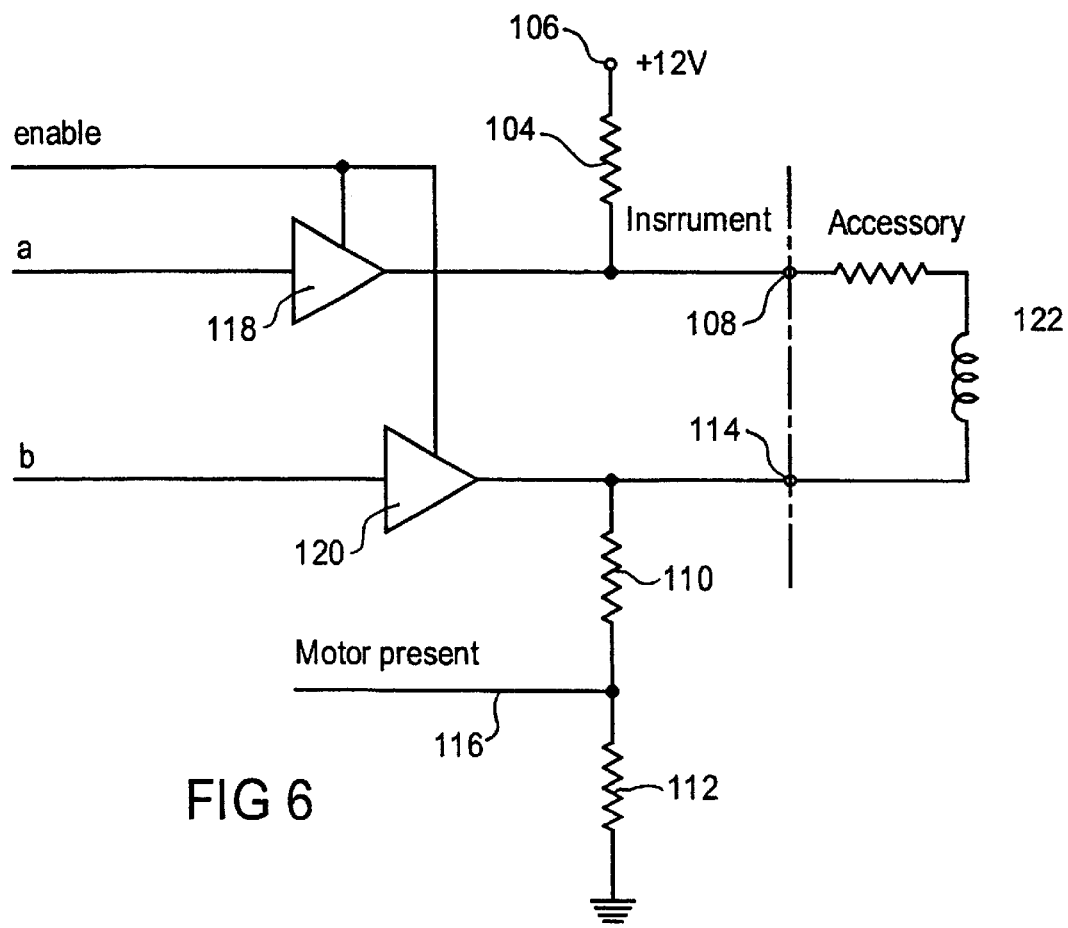

For an accessory with a stepper motor, the recognition circuitry may comprise a pull-up resistor 104 (see FIG. 6) connected between a voltage source 106 (eg. 12V) of the instrument and a pin 108 of the accessory socket. A voltage divider comprising resistors 110, 112 is connected between another pin 114 of the socket and ground. A signal line 116 is connected between the voltage divider resistors 110, 112. Motor drivers 118, 120 are connected to the pins 108, 114. FIG. 6 shows a motor of an accessory having a winding 122 connected across the pins 108, 114. On power up the motor drivers 118, 120 are disabled and pull up resistor 104 and voltage divider 110–112 generate a "motor present" signal, that is, if there is a motor winding connected across pins 108, 114 a current flows through the voltage divider 110–112 which generates a logic high signal (indicating "motor present") which is read by the microprocessor (not shown) to which signal line 116 leads. If a motor is not present, a logic low signal on line 116 is read by the microprocessor.

The plug of an accessory may be arranged on the accessory such that it automatically mates with a socket of the instrument as the accessory is attached thereon via a mechanical attachment mechanism as described hereinabove. Thus the one action of attaching an accessory may automatically establish its electrical connection to the instrument and completion of the recognition circuitry and the possible consequential automatic loading of programmes.

Figure 7A:
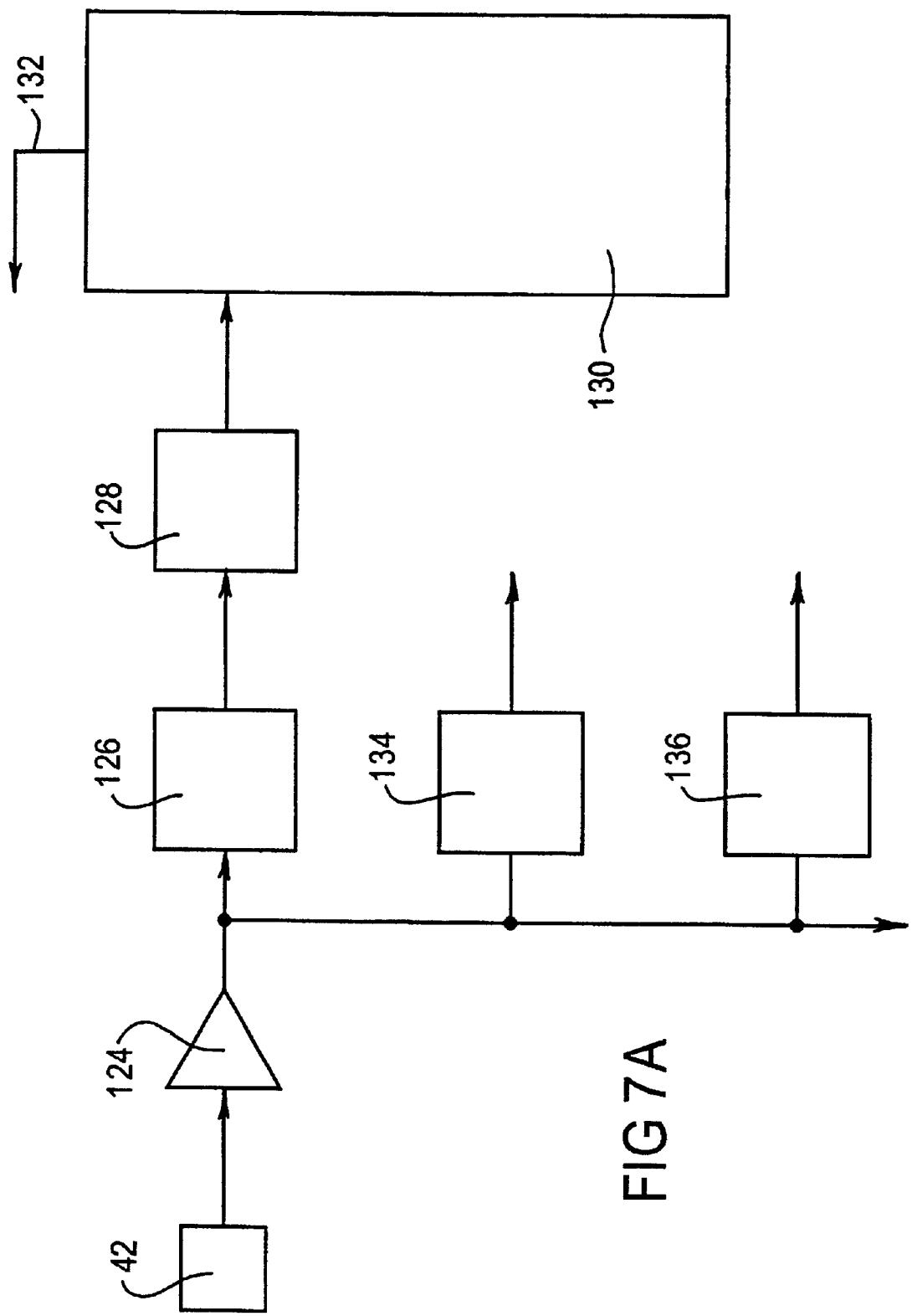

A data acquisition circuit of an instrument as in FIG. 1 is diagrammatically illustrated in FIG. 7A. This circuit comprises an amplification stage 124 connected to a detector 42 as in FIG. 1. The output of the amplification stage 124 is connected to a sample and hold circuit 126, the output of which is i connected to an analog to digital converter 128 which supplies the data to a microprocessor of a computer 130. The instrument is computer controlled and this is represented by line 132 (alternatively the instrument may be controlled by a dedicated device or circuitry). Multiple channel data acquisition circuits may be provided, or as illustrated, separate sample and hold circuits 134, 136 etc, each followed by an analog to digital converter {not shown)

may be connected between the amplification stage 124 and the computer 130. FIG. 78 illustrates a modification of the FIG. 7A circuit, namely the addition of control circuitry 138 which receives a signal on line 140 from an AID converter 128 indicating that a conversion is complete and sending a signal on line 142 to a sample and hold circuit 126, 134, 136 to start another conversion. That is, the additional circuitry 138–142 determines the measurement time dynamically, typically initiating the next conversion whenever one of the conversion circuits becomes idle.

Use of a fluorescence spectrophotometer as in FIG. 1 having a data acquisition circuit as in FIG. 7 and which may have either or both of the accessory attachment and accessory recognition features described hereinabove, for making phosphorescence measurements will now be described to exemplify the third aspect of the invention.

A problem with a data acquisition circuit such as that of FIG. 7A or 7B is that the gate time for the digitisation and reading of a sample data point from the sample and hold circuit 126 by the analog to digital converter 128 and microprocessor 130 usually exceeds the time space in between the data points which is necessary to adequately define the phosphorescence decay characteristic of the sample. That is, the electronics is not fast enough to convert all of the necessary data, hence a relatively high number of flash and read cycles have to be performed, with only one data point being collected for each cycle.

The controlled times between the phosphorescence emission measurement points for a particular excitation flash may be equal, with the time to the first measurement point resulting from the second excitation flash being different to and preferably longer than the time to the first measurement point resulting from the first excitation flash. Continuing with this sequence, the time to the first measurement point resulting from a third excitation flash will be greater than the time to the first measurement point resulting from the second excitation flash, and likewise for any subsequent excitation flashes.

Effectively the time to the first phosphorescence measurement points resulting from the first and subsequent excitation flashes are respectively offset such that the first measurement point resulting from the second excitation flash follows the first measurement point resulting from the first excitation flash, and the first measurement point resulting from a ti"1ird excitation flash follows the first measurement point resulting from the second excitation flash, and likewise for any subsequent excitation flashes.

The controlled time periods may be such that the interleaved data points are separated by equal time intervals. Alternatively the controlled time periods may be such that the interleaved data points are separated by unequal time periods. That is, this third aspect of the imention encompasses an operator being able to decide the particular time intervals that will exist between successive interleaved data points which define the phosphorescence decay characteristic. These particular time intervals may be equal or unequal and varied, as the operator determines.

Figure 8:
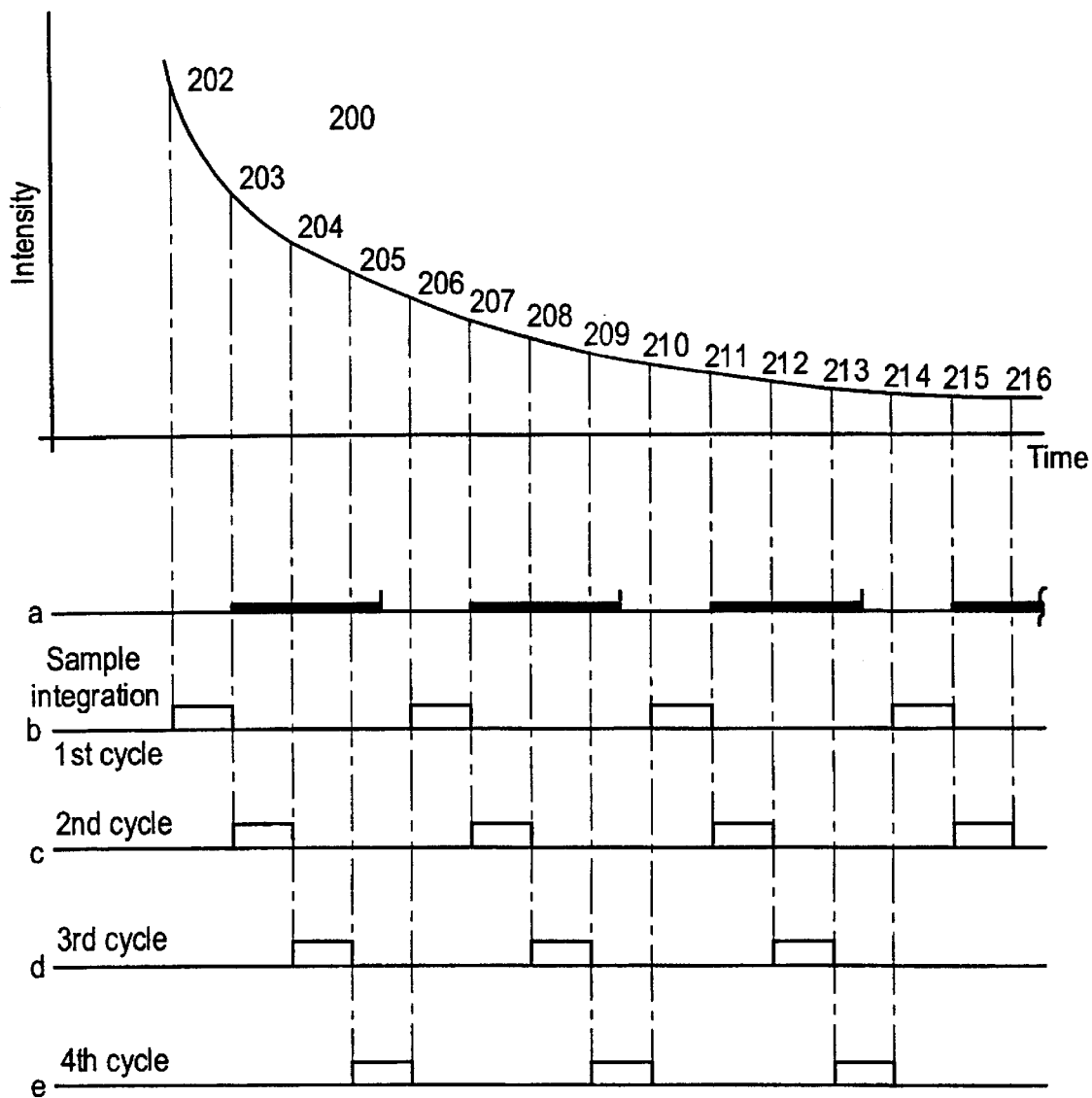
FIG. 8 diagrammatically illustrates a phosphorescence measurement regime.

FIG. 8 illustrates a phosphorescence decay characteristic 200 (intensity vs. time) for a sample for which it is desired that measurement data at points 202–215 be collected to define the characteristic. Sample integration periods for the data points 202–216 are shown at time-lines (b), (c), (d) and (e). The time intervals shown along time-line (a) represent the time for the data of a measurement point to be transferred to the computer. This time is greater than the spacing between the data points 202–21), thus the computer cannot collect the data of all the desired measurement points in one pass.

According to the invention, several decay scans are performed and the data from each are interleaved in a correct time sequence to derive the phosphorescence decay characteristic. The measurement regime is under control of computer 130 which keeps track of all the delay/emission data points required to define the phosphorescence decay characteristic. Following an excitation flash, the data acquisition electronics 42–124–126–128–130 completes collection of the first datum 202 as represrented by time interval at (a), the computer notes the time from the excitation pulse, looks for the next unmeasured point 206 after that time and triggers the data acquisition electronics to collect that point as well, and so on for the illustrated datums 210 and 214. Thus several data points are measured on the one cycle as shown at (b). The next excitation pulse is then triggered, and under the control of the computer, the data points 203, 207, 211, 215 are collected, as shown at (c) and so on for as many cycles as are required to collect all the desired data points, see (d) and (e).

The computer then assembles all the measured data points into the correct overall time sequence to create the complete phosphorescence characteristic. For example, if measurement at 1 microsecond intervals is required to define the phosphorescence ch.3racteristic and the acquisition of each measurement data point takes 19.5 microseconds, on the first cycle the emission at 1 microsecond is measured. This data is transferred to the computer at 20.5 microseconds. The next data point required is at 21 microseconds so the computer triggers the electronics to collect this point. The second point is transferred to the computer at time 40.5 microseconds. The next data point required is at 41 microseconds and so the computer triggers the electronics to collect this point, and so on. On the second cycle, the computer collects data for times 2 microseconds, 22 microseconds, 42 microseconds etc. In this example, for data covering 2 milliseconds, all points can be collected in 20 cycles instead of 2000 cycles for the prior art approach, reducing the overall measurement time from 20 seconds to 200 milliseconds.

The time intervals between the data points may vary or be fixed and is not critical to the invention, which is characterised by the collection of more than one data point from each cycle and the reassembly of those data points into the correct time sequence within the associated computer system.

This third aspect of the invention offers several advantages. The first is the time saving leading to increased productivity. Some samples have the characteristic of changing their properties with time or with the amount of excitation light received. The invention reduces both the measurement and the total integrated amount of excitation light imposed on the sample thereby minimising this source of measurement uncertainty.

In order to obtain good time precision for short duration 15 phosphorescence events the duration of the excitation pulse needs to be short while at the same time delivering a high total I light flux to the sample. A xenon flash lamp 20 meets these requirements of short duration and high intensity and is thus a desirable source for such applications. It has however the disadvantage that the light output per flash is variable. Since the emission signal is proportional to the excitation signal such variation must be allowed for if accurate results are to be obtained. To this end, in the implementation of the phosphorescence measurement method, the excitation flux for each pulse is measured at the start of each cycle and used to normalise the emission measurements collected during that cycle. That is, as is known, a dark signal is measured for the sample for each cycle, and a dark signal and reference signal for the reference beam 30 which are used to normalise the results.

A further variant on this third aspect is to use two or more independent sets of measurement and digitisation electronics operating from the same signal source and all capable of transmitting the digitised value to the processor. In this case the processor initiates a first excitation flash of light and as each measurement time instant is reached it triggers the next available set of measurement and digitisation electronics to acquire the value. This variant has the advantage of achieving still shorter data collection times but at the expense of greater electronic cost and complexity. Thus two or more independent sets of digitisation electronics may be used in conjunction with multiple flashes to give still greater speeds.

Preferably a reference intensity measurement is taken of every excitation flash of light, and the phosphorescence emission intensity measurements derived from that flash are ratioed with the reference to compensate for differences in intensity which may occur between flashes. As is known such compensation may include dark signal measurements being taken immediately before an excitation flash and subtracted from the measured excitation and emission intensities for the ratioing.

The invention in each of its aspects as described herein is susceptible to variations, modifications and/or additions other than those specifically described and it is to be understood that the invention includes all such variations, modifications and/or additions which fall within the scope of the following claims.

What is claimed is:

1. A method of determining a phosphorescence decay characteristic of a sample, or at least a portion thereof, comprising the steps of
   i) exposing the sample to a first excitation flash of light,
   ii) measuring the intensity of a decaying phosphorescence light signal from the sample caused by the first excitation flash at each of a sequence of measurement points which commence at a controlled time after the first excitation flash and are separated by controlled time intervals,
   iii) exposing the sample to a second excitation flash of light, and
   iv) measuring the decaying phosphorescence light signal from the sample caused by the second excitation flash at each of a sequence of measurement points which commence at a controlled time interval after the second excitation flash and are separated by controlled times,
   v) assembling the phosphorescence measurements into time sequence to produce a phosphorescence decay characteristic, or a portion thereof, for the sample.

2. A method as claimed in claim 1 including repeating steps (iii) and (iv) in respect of further excitation flashes of light, respectively, wherein the further phosphorescence measurements for each such further excitation flash are taken after controlled intervals such that in step (v) each said further phosphorescence measurement is interleaved between phosphorescence measurements resulting from earlier excitation flashes.

3. A method as claimed in claim 1 wherein the controlled times are such that the time intervals between the assembled phosphorescence measurements of step (v) are equal.

4. A method as claimed in claim 1 wherein the controlled times are such that the time intervals between the assembled phosphorescence measurements of step (v) vary from one internal to the next.

5. A method as claimed in claim 1 wherein the controlled time intervals separating the initial and subsequent measurement points of the decaying phosphorescence light signal from, respectively, the first and second and any subsequent excitation flashes are determined prior to commencement of the method.

6. A method as claimed in claim 1 wherein the controlled times separating the first and subsequent measurement points of the decaying phosphorescence light signal from, respectively, the first and second and any subsequent excitation flashes are determined during the method.

7. A method as claimed in claim 6 wherein the controlled time between successive measurement points of the decaying phosphorescence signal caused by an excitation flash is determined to be greater than a time for measurement and digitization of data from a previous measurement point.

8. The method as claimed in claim 1 wherein the time delays to the initial measurement point from the second excitation flash are later than the time delay to the initial point respectively from the first excitation flash.

9. Apparatus for determining a phosphorescence decay characteristic of a sample or at least a portion thereof comprising a spectrophotometer and a means for controlling the spectrophotometer, wherein the means for controlling is arranged to acquire sequential phosphorescence emission measurements data from each of a number of excitation cycles applied to a sample in the spectrophotometer and to assemble that data into a a uniformly increasing time sequence to define a phosphorescence time decay characteristic, or portion thereof, for the sample.

10. Apparatus as claimed in claim 9 wherein the spectrophotometer includes a data acquisition circuit for acquiring the sequential phosphorescence emission measurements data, the data acquisition circuit including a sample and hold stage followed by an analog to digital conversion stage from which the data is acquired by the means for controlling, wherein the means for controlling is arranged for sequential phosphorescence emission measurements from each excitation cycle to be taken at time intervals relative to the excitation which are longer than the time required for conversion of a measured datum to occur in the analog to digital conversion stage and be acquired by the means for controlling the spectrophotometer.

11. Apparatus as claimed in claim 9 wherein the spectrophotometer includes a plurality of data acquisition circuits for acquiring the sequential phosphorescence emission measurements data, each said data acquisition circuit including a sample and hold stage, each said sample and hold stage followed by an analog to digital conversion stage from which the data is acquired by one selected said data acquisition circuit through selection by the means for controlling, wherein the means for controlling is arranged for sequential phosphorescence emission measurements from each excitation cycle to be taken at time intervals relative to the respective excitation which are longer than the time required for conversion of a measured datum to occur in an analog to digital conversion stage and be acquired by the means for controlling the spectrophotometer.

12. Apparatus as claimed in claim 11 wherein the means for controlling is arranged for an initial measurement of phosphorescence emission from the first and subsequent excitation cycles to be respectively offset in time such that the initial measurement resulting from a second excitation cycle follows the initial measurement resulting from a first excitation cycle, and the initial measurement resulting from a third excitation cycle follows the initial measurement resulting from the second excitation cycle, and likewise for subsequent excitation cycles, said means for controlling selects one said data acquisition circuit to perform one said measurement and selects another said data acquisition circuit to perform a subsequent measurement for same said excitation cycle, whereby the assembly of the measurements data into a correct time sequence results in the measurements from the second and subsequent excitation cycles being interleaved with the measurements from the first excitation cycle.

13. Apparatus for determining a phosphorescence decay characteristic of a sample or at least a portion thereof comprising a spectrophotometer and a means for controlling the spectrophotometer, wherein the means for controlling is arranged to acquire sequential phosphorescence emission measurements data from each of a number of excitation cycles applied to a sample in the spectrophotometer and to assemble that data into a uniformly increasing time sequence to define a phosphorescence time decay characteristic, or portion thereof, for the sample, wherein the spectrophotometer includes a data acquisition circuit for acquiring the sequential phosphorescence emission measurements data, the data acquisition circuit including a sample and hold stage followed by an analog to digital conversion stage from which the data is acquired by the means for controlling, wherein the means for controlling is arranged for sequential phosphorescence emission measurements from each excitation cycle to be taken at time intervals relative to the excitation which are longer than the time required for conversion of a measured datum to occur in the analog to digital conversion stage and be acquired by the means for controlling the spectrophotometer, wherein the means for controlling is arranged for initial measurement of phosphorescence emission from the first and subsequent excitation cycles to be respectively offset in time such that the initial measurement resulting from a second excitation cycle follows the initial measurement resulting from a first excitation cycle, and the initial measurement resulting from a third excitation cycle follows the first measurement resulting from the second excitation cycle, and likewise for subsequent excitation cycles, whereby the assembly of the measurements data into a uniformly increasing time sequence results in the measurements from the second and subsequent excitation cycles being interleaved with the measurements from the first excitation cycle.

14. Apparatus as claimed in claim 13 wherein the means for controlling the spectrophotometer is a programmable computer.

* * * * *